United States Patent [19]

Dessau

[11] Patent Number: 4,704,495

[45] Date of Patent: Nov. 3, 1987

[54] CATALYTIC CONVERSIONS USING SHAPE SELECTIVE METALLIC CATALYSTS

[75] Inventor: Ralph M. Dessau, Edison, N.J.

[73] Assignee: Mobil Oil Corporation, New York, N.Y.

[21] Appl. No.: 841,929

[22] Filed: Mar. 20, 1986

Related U.S. Application Data

[63] Continuation of Ser. No. 456,919, Jan. 10, 1983, abandoned, which is a continuation-in-part of Ser. No. 220,677, Dec. 29, 1980, Pat. No. 4,377,503.

[51] Int. Cl.$^4$ ............................ C07C 5/22; C07C 5/27
[52] U.S. Cl. .................................. 585/481; 585/419; 585/627; 208/111; 208/120
[58] Field of Search .......................................... 585/481

[56] References Cited

U.S. PATENT DOCUMENTS

| | | | |
|---|---|---|---|
| 3,525,775 | 8/1970 | Bolton et al. | 585/481 |
| 3,575,845 | 4/1971 | Miale | 208/111 |
| 4,086,287 | 4/1978 | Kaeding | 585/466 |
| 4,128,592 | 12/1978 | Kaeding | 585/467 X |
| 4,159,282 | 6/1979 | Olson et al. | 585/481 |
| 4,159,283 | 6/1979 | Nicoletti et al. | 585/481 |
| 4,356,338 | 10/1982 | Young | 585/407 |
| 4,385,195 | 5/1983 | Butter et al. | 585/481 |
| 4,431,746 | 2/1984 | Rollmann | 507/73 |
| 4,508,836 | 4/1985 | Haag et al. | 502/53 |
| 4,552,855 | 11/1985 | Ozin et al. | 502/74 |

*Primary Examiner*—Olik Chaudhuri
*Attorney, Agent, or Firm*—Alexander J. McKillop; Michael G. Gilman; Dennis P. Santini

[57] ABSTRACT

A novel shape selective metal catalyst can be prepared by incorporating a metallic catalyst component such as platinum, palladium, or nickel into a member of a novel class of zeolites, said zeolites characterized by a silica to alumina mole ratio of at least 12 and a constraint index within the approximate range of 1 to 12, and then reducing the combined metal-zeolite in the presence of unsaturated hydrocarbon compounds with or without hydrogen at high temperatures.

12 Claims, No Drawings

4,704,495

CATALYTIC CONVERSIONS USING SHAPE SELECTIVE METALLIC CATALYSTS

CROSS-REFERENCE TO RELATED APPLICATION

This is a continuation of application Ser. No. 456,919, filed Jan. 10, 1983, now abandoned which is a continuation-in-part of application Ser. No. 220,677, filed Dec. 29, 1980, now U.S. Pat. No. 4,377,503.

BACKGROUND OF THE INVENTION

1. Field of the Invention

This invention relates to a novel shape selective metal catalyst, a method of preparing same and its employment in various catalytic processes.

2. Description of the Prior Art

Shape selective catalysis utilizing molecular sieves was first demonstrated by P. B. Weisz and V. J. Frilette in *J./Phys. Chem.* 64, p. 302 (1960). Since then, the shape selective catalytic properties of various zeolites have been extensively demonstrated. For example, N. Y. Chen and W. E. Garwood in "Some Catalytic Properties of ZSM-5, a New Shape Selective Zeolite", *Journal of Catalysis*, 52, p. 453–458 (1978) described the shape selectivity of ZSM-5. On the other hand, tne use of zeolites as shape-selective supports for catalytic functions has received much less attention.

P. B. Weisz, V. J. Frilette, R. W. Maatman and F. B. Mower in "Catalysis by Crystalline Aluminosilicates II. Molecular-Shape Reactions", *Journal of Catalysis*, 1, p. 307–312 (1962) described a shape selective olefin hydrogenation catalyst comprising platinum incorporated in zeolite A. In U.S. Pat. No. 3,140,322 of V. J. Frilette and P. B. Weisz, a process is disclosed for hydrogenation using a platinum containing zeolite. In U.S. Pat. No. 3,226,339 of V. J. Frilette and R. W. Maatman, a process is described for the preparation of a platinum or palladium containing zeolite catalysts. U.S. Pat. No. 3,575,045 of J. N. Miale discloses the use of a platinum entrained zeolite A for selective hydrogenation.

A catalyst and process for selectively hydrogenating ethylene in the presence of propylene utilizing a zeolite in conjunction with a hydrogenation metal is disclosed in U.S. Pat. No. 3,496,246. N.Y. Chen and P. B. Weisz in "Molecular Engineering of Shape-Selective Catalysts", *Kinetics and Catalysis, Chem. Eng Prog. Symp.* Ser. No. 73, Vol. 63, 1967, p. 86, described a platinum catalyzed hydrogenation employing a phosphine-poisoned platinum-exchanged sodium mordenite zeolite.

An excellent summary of the art of metal loaded zeolite catalysts and shape selective catalysis is given in *Zeolite Chemistry and Catalysts*, J. A. Rabo, ed., ACS Monograph 171 (1976). Of particular interest is Chapter 10, "Catalytic Properties of Metal-Containing Zeolites" by K. M. Minachev and Y. I. Isakov and Chapter 12, "Shape-Selective Catalysis" by S. M. Csicsery, the entire contents of which are herein incorporated by reference.

Heretofore, a shape selective metallic catalyst has not been prepared in which one metal function is incorporated into a zeolite characterized by a silica to alumina mole ratio of at least 12 and a constraint index, as hereinafter defined, in the approximate range of 1 to 12, e.g., ZSM-5 zeolite.

SUMMARY OF THE INVENTION

In accordance with the present invention, there is now provided a novel shape selective metal catalyst and a method to prepare same. Shape selectivity is imparted to such metal catalyst components as platinum, palladium and nickel, etc. via utilization of members of a novel class of zeolites and by novel reduction techniques. Said class of zeolites is characterized by a silica to alumina mole ratio of at least 12 and a constraint index in the appropriate range of 1 to 12.

The preparation of the novel shape selective metal catalyst is accomplished by incorporating the metal catalyst component into a member of the aforesaid novel class of zeolites and then reducing the metal loaded zeolite at elevated temperatures in the presence of one or more unsaturated hydrocarbon compounds and with or without hydrogen. It will be appreciated that reduction of such metal catalysts is required to activate them. The prior art taught such reduction only in a hydrogen atmosphere or reduction using oxygen followed by hydrogen. Reduction in hydrogen alone, without added unsaturated hydrocarbons such as olefins, will result in an active, but non-shape selective catalyst.

DESCRIPTION OF PREFERRED EMBODIMENTS

A shape selective metal catalyst can be prepared according to this invention by incorporating a metal catalyst component into a member of the novel class of zeolites and then reducing the metal loaded zeolite at elevated temperatures in the presence of unsaturated hydrocarbons, particularly olefins, with or without hydrogen. The preferred metal catalyst components useful herein are selected from the Group VIII metals in the Periodic Table including platinum, palladium and nickel, with platinum particularly preferred.

The crystalline zeolites utilized in the particular embodiment members of a novel class of zeolite materials which exhibit unusual properties. Although these zeolites have unusually low alumina contents, i.e. high silica to alumina mole ratios, they are very active for many reactions, e.g. cracking, even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, or possibly other elements) atoms at the centers of the tetrahedra. It should be understood that the "zeolites" of the present invention are not limited to those which contain both silicon and aluminum.

For the purpose of this invention, the term "zeolite" is meant to represent the class of porotectosilicates, i.e., porous crystalline silicates that contain silicon and oxygen atoms as the major components. Other components may be present in minor amounts, usually less than 14 mole % and preferably less than 4 mole %. These components include aluminum, gallium, iron, boron and the like with aluminum being preferred and used herein for illustration purposes. The minor components may be present separately or in mixtures.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolite with a silica to alumina mole ratio of at least 12 are useful, it is preferred in some instances to use zeolites having much higher silica to alumina mole ratios. In addition, zeolites as otherwise characterized herein but which are substantially free of aluminum, i.e. having silica to alumina mole ratios up to and including infinity, are found to be useful and even preferable in some instances. Such "high silica" zeolites are intended to be included within this description. The novel class of zeolites, after activation, acquire an intra-crystalline sorption capacity for normal hexane which is greater than that for water, i.e. they exhibit "hydrophobic" properties.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. (1005° F.) for at least 15 minutes. The zeolite is then flushed with helium and the temperature is adjusted between 290° C. (555° F.) and 510° C. (950° F.) to give an overall conversion of between 10% and 60%. The mixture of hydrocarbons is passed at 1 liquid hourly space velocity (i.e. 1 volume of liquid hydrocarbon per volume of zeolite per hour) over the the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10% to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. (1005° F.) and a liquid hourly space velocity (LHSV) of less than one, such as 0.1 or less, can be employed in order to achieve a minimum total conversion of about 10%.

There also may be instances where the activity is so low (i.e. silica to alumina mole ratio approaching infinity) that the constraint index cannot be adequately measured, if at all. In such situations, Constraint Index is meant to mean the Constaint Index of the exact same substance (i.e. same crystal structure as determined by such means as X-ray diffraction pattern) but in a measureable form (i.e. aluminum containing form).

The "Constraint Index" is calculated as follows:

$$\text{Constraint Index} = \frac{\log 10(\text{fraction of hexane remaining})}{\log 10(\text{fraction of 3-methylpentane remaining})}$$

The Constraint Index approximates the ratio of the cracking rate constants for the two hydrocarbons. Zeolites suitable for the present invention are those having a Constraint Index in the appropriate range of 1 to 12.

Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 1.5 |
| H-Zeolcon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the approximate range of 1 to 12 for the Constraint Index of a particular zeolite. Such a zeolite exhibits the constrained access as herein defined and is to be regarded as having a Constraint Index in the approximate range of 1 to 12. Also contemplated herein as having a Constraint Index in the approximate range of 1 to 12 therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the approximate range of 1 to 12 is intended to be included in the instant novel zeolite definition whether or not the same identical zeolite, when tested under other of the defined conditions, may give a Constraint Index value outside of the approximate range of 1 to 12.

The novel class of zeolites defined herein is exemplified by ZSM-5, ZSM-11, ZSM-5/ZSM-11 intermediate, ZSM-12, ZSM-23, ZSM-35, ZSM-38, ZSM-48, and other similar materials.

ZSM-5 is described in greater detail in U.S. Pat. No. 3,702,886 and Re. No. 29.949. The entire descriptions contained within those patents, particularly the X-ray diffraction pattern of the therein disclosed ZSM-5, and is incorporated herein by reference.

ZSM-11 is described in U.S. Pat. No. 3,709,979. That description, and in particular the X-ray diffraction pattern of said ZSM-11, is incorporated herein by reference.

ZSM-5/ZSM-11 intermediate is described in U.S. Pat. No. 4,229,424, the entire contents of which is incorporated herein by reference.

ZSM-12 is described in U.S. Pat. No. 3,832,449. That description, and in particular the X-ray diffraction pattern of said ZSM-12, is incorporated herein by reference.

ZSM-23 is described in U.S. Pat. No. 4,076,842. The entire content thereof, particularly the specification of the X-ray diffraction pattern of the disclosed zeolite is incorporated herein by reference.

ZSM-35 is described in U.S. Pat. No. 4,016,245. The description of that zeolite, and particularly the X-ray diffraction pattern thereof, is incorporated herein by reference.

ZSM-38 is described in U.S. Pat. No. 4,046,859. That description, and particularly the X-ray diffraction pattern of said ZSM-38, is incorporated herein by reference.

ZSM-48 is described in U. S. Pat. No. 4,397,827. That description, and particularly the X-ray diffraction pattern of said ZSM-48, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalyts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are unsuitable for use herein, possibly because tne intracrystalline free space is occupied by organic cations from the forming solution. They may be made suitable by heating in an inert atmosphere at 540° C. (1005° F.) for one hour. If desired, these zeolites may then be ion exchanged with suitable compounds, e.g. salts, to get desired cationic form, e.g. sodium, hydrogen, ammonium, etc. The presence of organic cations in the forming solution may not be absolutely essential to the formation of this type zeolite; however, the presence of these cations does appear to favor the formation of this special class of zeolite.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 and ZSM-11 being particularly preferred.

The crystalline zeolites of the present invention generally have a minimum crystal dimension of about 0.01 micron. Preferably, however, zeolites with a crystal dimension of greater than about 0.1 micron are employed.

In a preferred aspect of this invention, the zeolites hereof are selected as those providing, among other things, a crystal framework density in the dry hydrogen form, of not less than about 1.6 grams per cubic centimeter. It has been found that zeolites which satisfy all three of the discussed criteria are most desired for several reasons. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstoms, as given, e.g., on Page 19 of the article ZEOLITE STRUCTURE by W.M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techiques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the focus of catalytic activity.

Crystal framework densities of some typical zeolites, including some which are not within the purview of this invention are:

|  | Void Volume | Framework Density |
|---|---|---|
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1 5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

The incorporation of the metallic catalyst component into the novel zeolite of this invention can be accomplished by any suitable means such as ion exchange. In some instances this ion exchange may prove difficult, in which case it may be desirable to form a complex of the metal before attempting the exchange. A particularly preferred method to ion exchange platinum and palladium metals into the zeolites of this invention is to employ an ammine complex of such metals. Such complex can be formed by first dissolving the metal in an acid, e.g. aqua regia, and then adding an amine such as ammonium hydroxide, i.e. ammonia solution, until the entire solution becomes basic. Alternatively, a salt of the metal, e.g. platinum chloride, can be contacted with amine solution, e.g. ammonia solution, until basic. The weight ratio of metallic catalyst component to zeolite is not critical, however, it is desirable to have a weight ratio in the range of between about 0.01% and about 10% and preferably between about 0.2% and about 5%.

Alternatively, the metallic catalyst component can be incorporated into the zeolite by impregnating the zeolite with a solution of the metal or metal compounds or complexes, followed by stripping of the solvent employed. Metallic component incorporation can also be accomplished by sorbing metal compounds or complexes into the zeolite. Thus, such materials as nickel carbonyl or rhodium carbonyl chloride can be sorbed from solution or from the gas phase into the zeolite structure.

Once the metal loaded zeolite catalyst is prepared, the catalyst is activated by reduction with unsaturated hydrocarbon compounds at a temperature of between about 100° C. (210° F.) and about 500° C. (930° F.) and preferably between about 150° C. (300° F.) and about 450° C. (840° F.). The unsaturated hydrocarbons must be maintained throughout the reduction at a concentration of between about 1% and about 100% and more preferably between about 10% and about 50%. Once reduction is complete, there is no longer a need for the presence of the unsaturated hydrocarbons. It is preferred that such reduction be conducted in a hydrogen atmosphere, however, the reduction can occur in the absence of hydrogen, e.g. olefin only, or olefin and inert gas (e.g., nitrogen).

In a preferred embodiment of this invention, a very stable catalyst can be achieved by back exchanging a bulky ion onto said catalyst prior to the aforementioned reduction. Non-limiting examples of such bulky ions include cesium and potassium.

The resultant catalyst of the method of this invention can be utilized in any process or combination of processes which employs metal catalyst components such as platinum, palladium, nickel and combinations thereof. Examples of such processes include hydrogenation, dehydrogenation, dehydrocyclization, isomerization, cracking, dewaxing, reforming, conversion of alkylaromatics, oxidation, etc.

It is noted that the particular advantage of the novel catalyst prepared by the method of this invention is its ability to catalyze specific reactions shape selectively. For example, by utilizing a platinum or palladium version of the catalyst of the instant invention straight-chain olefins will be selectively hydrogenated over branched-chain olefins. Tne resultant catalyst also exhibits very good stability in the presence of poisons, e.g. sulfur, phosphorus, as well as having enhanced high temperature activity (see Table 3 hereinbelow). It is also postulated that the catalyst produced by the novel method of this invention would be less susceptible to coking. Thus the resultant catalyst would also be applicable in metal catalyzed reactions in which shape selectivity is not per se crucial, e.g., oxidation, reforming, synthesis gas conversion, hydroformylation, dimerization, polymerization, alcohol conversion, etc.

Catalytic conversion conditions for hydrogenation of such feedstocks as alkenes, dienes, polyenes, alkynes, cyclenes, aromatics, oxygenates, etc. include a temperature of between about −20° C. (−4° F.) and about 540° C. (1005° F.), preferably between about 25° C. (77° F.) and 310° C. (590° F.), a pressure of between about 100 kPa (0 psig) and about 7800 kPa (1000 psig), preferably between about 100 kPa (0 psig) and 1480 kPa (200 psig), a hydrogen/feed mole ratio of between about 0.1 and 20, preferably between about 4 and 12 and a LHSV of between about 0.1 and 100, preferably between about 0.5 and 4.

Dehydrogenation conditions, for example for conversion of paraffins to the corresponding olefins or ethyl benzene to styrene, optionally in the presence of steam or inert gases such as nitrogen, include temperatures of from about 200° C. (392° F.) to 1000° C. (1832° F.), preferably from about 350° C. (662° F.) to 600° C. (1112° F.); feedstock partial pressures of from about 10 kPa (1.5 psia) to 10,000 kPa (1470 psia), preferably from about 10 kPa (1.5 psia) to 100 kPa (14.7 psia) and a LHSV of from about 0.1 to 100, preferably between aoout 0.5 and 4.

Dehydrocyclization conditions, for example for conversion of paraffins to aromatics (e.g. octane to ethylbenzene or xylene), also include temperatures of from about 200° C. (392° F.) to 1000° C. (1832° F.), preferably from about 350° C. (662° F.) to 600° C. (1112° F.); feedstock partial pressures of from about 10 kPa (1.5 psia) to 10,000 kPa (1470 psia), preferably from about 10 kPa (1.5 psia) to 100 kPa (14.7 psia) and a LHSV of from about 0.1 to 100, preferably between about 0.5 and 4.

Isomerization, with or without hydrogen, such as isomerization of normal paraffins, is conducted at a temperature of between about 100° C. (212° F.) and 500° C. (932° F.), preferably between about 150° C. (300° F.) and 290° C. (550° F.), a LHSV of between about 0.01 and 50, preferably between about 0.25 and 5 and a hydrogen to hydrocarbon mole ratio of between 0 and 5:1.

Catalytic conversion conditions for cracking, with or without hydrogen, include a temperature of between about 200° C. (400° F.) and about 500° C. (932° F.), a pressure of between about 170 kPa (10 psig) and about 17,600 kPa (2500 psig), a hydrogen/feed mole ratio of between about 0 and about 80 and a LHSV of between about 0.1 and about 10.

The shape selective catalysts of the present invention are also useful in dewaxing operations and can likewise be employed as reforming catalysts or as part of a reforming catalyst. Dewaxing and reforming can be carried out in the presence or absence of hydrogen under conditions which include a temperature of from about 250° C. (482° F.) to 600° C. (1112° F.), preferably from about 400° C. (752° F.) to 500° C. (932° F.); a pressure of from about 10 kPa (1.5 psia) to 10,000 kPa (1470 psia) and a WHSV of from about 0.01 to about 100, preferably from about 0.1 to 10.

Catalytic conversion conditions for conversion of alkylaromatics including dealkylation or hydroisomerization, particularly xylene isomerization and hydroisomerization of ethylbenzene to xylene, include a temperature of between about 260° C. (500° F.) and about 600° C. (1112° F.), preferably between about 320° C. (600° F.) and 500° C. (932° F.), a pressure of between about 240 kPa (20 psig) and about 7000 kPa (1000 psig), preferably between about 275 kPa (25 psig) and about 2860 kPa (400 psig), a hydrogen/feed mole ratio of between about 1 and 20, preferably between about 2 and about 8 and a WHSV of between about 1 and 50, preferably between about 5 and 15.

The metal containing catalysts of the present invention can also be advantageously employed under oxidation reaction conditions as oxidation or combustion catalysts. Thus, the novel catalysts of the present invention can be employed for oxidation reactions such as oxidation or combustion of paraffins, olefins and alkylaromatics and in processes involving reaction of CO and $H_2$ (methanol synthesis, Fischer-Tropsch process, etc.) wherein shape selectivity is not necessarily essential. Such catalysts can also shape selectively catalyze oxidation reactions such as, for example, the selective oxidation of p-xylene relative to o-xylene.

The metal containing catalyst produced according to the method of the instant invention represents a novel catalyst composite. The catalyst of this invention differs from prior art catalysts in that the instant catalyst is shape selective. Without wishing to be bound by any particular theory of operability, it is believed that the shape selectivity of the present catalyst is due to the position of the metal function "inside" (rather than "outside") the zeolite with the metal function having a valence of zero (rather than having a positive valence). In the case of a Pt-ZSM-5 catalyst composite, prior art techniques involving ion exchange would result in $Pt^{+2}$ being inside the zeolite, not Pt°. Upon reduction, the $Pt^{+2}$ would migrate to the surface and form Pt°. Thus prior art techniques would result in either $Pt^{+2}$ inside the zeolite or Pt° on the surface of the zeolite, but not Pt° inside, i.e. in the interstices of the zeolite.

The shape selective metal catalyst of the present invention is characterized as having a selectivity of greater than 2.0 for the selective hydrogenation of a linear olefin, e.g. hexene-1, over a dimethyl branched olefin, e.g., 4,4-dimethylhexene-1. Such selectivity can be determined in a standard competitive olefin hydrogenation test. In such a test, a 1:1 molar mixture of the straight and branched chain olefins and hydrogen are passed through a down-flow fixed bed glass reactor containing from about 5 mg to 30 mg, e.g. 15 mg, of the catalyst being tested after ammonia injection to supress acidity. Using a 5-fold excess of hydrogen over olefin, hydrogenation is carried out at a temperature of from about 200° C. (392° F.) to 480° C. (895° F.), e.g. about 300° C. (575° F.), using a WHSV of from about 5 to 100, e.g. 25. Percent hydrogenation of each of the two olefins is measured and selectivity is calculated according to the following equation based on the percentage of each olefin left unconverted to the hydrogenation product.

$$\text{Selectivity} = \frac{\ln (\% \text{ Branched Olefin Unconverted})}{\ln (\% \text{ Linear Olefin Unconverted})}$$

As noted hereinbefore, shape selective characteristics can be imparted to the metal containing catalysts of the present invention by reducing a metal containing zeolite in the presence of one or more unsaturated compounds. The shape selectivity of such catalysts metals can be increased even further by means of several additional zeolite treatment operations. Selectivity can be increased, for example, by increasing the temperature of the shape selective conversion reactions, e.g. hydrogenation, being carried out. Shape selectivity of the catalysts of the present invention can also be increased by selectively poisoning the catalyst with a "bulky" poison such as tri-p-tolylphosphine. Such bulky poisons deactivate the metallic catalyst component on the "outside" of catalyst composite to a greater extent than they poison the metal function in the interstices of the composite.

The following examples will serve to illustrate the invention without limiting same.

EXAMPLE 1

This example illustrates the preparation of $NH_4$-ZSM-5 zeolite with a crystal size of about 1 to 2 microns.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W.R. Grace Chem. Co.) The solution was cooled to approximately 15° C.

An acid solution was prepared by adding 1 part aluminum sulfate (17.2 wt % $Al_2O_3$) to 16.4 parts water followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:
$SiO_2/Al_2O_3 = 78.4$
$Na_2O/Al_2O_3 = 49.9$ An organic solution was prepared by adding 1.6 parts n-propyl bromide and 3.1 parts methyl ethyl ketone to 1.9 parts tri-n-propylamine and added to the gel.

The mixture was reacted at 65°-70° C. (150°-160° F.) with severe agitation for 29 hours.

The zeolite slurry product was diluted with 4-5 parts water per part slurry and 0.002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the decant supernatant liquid was $Cl^-$ free. The washed zeolite was then filtered, dried and identified as ZSM-5 having a silica/alumina mole ratio of about 70, and a constraint index of about 8.3. The ammonium form of the zeolite was obtained by calcination and $NH_4NO_3$ exchange.

EXAMPLE 2

A sample of Pt-ZSM-5 catalyst was prepared by exchanging $NH_4$-ZSM-5, prepared according to Example 1, containing 0.354 meq N/gram zeolite, with CsCl. The resultant Cs-ZSM-5 analyzed for only 0.013 residual meq N/g. 4 grams of this Cs-ZSM-5 was mixed with 1.25 g $Pt(NH_3)_4Cl_2 \cdot H_2O$ dissolved in 50 ml water and stirred for four hours at room temperature.

Titration of the effluent gases produced in the thermal gravimetric analysis of this material in hydrogen indicated the presence of 0.618 meq N/q, which is equivalent to 88% exchange with $Pt(NH_3)_4^{+2}$ ions.

EXAMPLE 3

1 g of the catalyst material from Example 2 was back-exchanged with an equal weight of CsCl dissolved in 20 ml of water. The resultant material analyzed for only 0.216 meq N/g. The resultant catalyst was Cs-Pt-ZSM-5 with the platinum content reduced to one-third of the original amount. The percentage of platinum in the catalyst was 1.0 wt. %.

EXAMPLES 4-7

The Cs-Pt-ZSM-5 catalyst prepared according to Example 3 was used in conjunction with a down-flow fixed bed glass reactor to conduct competitive hydrogenation reactions. The reactor was connected to an on-line gas chromatograph, containing a 12 foot n-octane Durapak column. To reduce the amount of cracking observed, a few cc of ammonia gas was injected prior to actual sampling. The amount of catalyst used ranged from between about 5 and 30 mg dispersed in 2 cc of vycor. The catalyst was activated in the reactor itself prior to use by reduction in a hydrogen stream, either in the presence or absence of added olefin at a temperature in the range of between about 300° C. (570° F.) and 480° C. (895° F.). The olefins were fed into the reactor by means of a syringe pump and diluted with a flow of hydrogen. Typical operating conditions included a hydrogen flow of 14 cc/min. and a liquid feed (olefin) rate of 1.0 cc/hr., which represented a 5-fold excess of hydrogen over olefin. When an olefin was used during reduction, an equimolar solution of two olefins were fed into the reactor. Examples 4-7 illustrate the effects of catalyst pretreatment on hydrogenation selectivity. The results for Examples 4-7 are qiven in Table 1.

In Example 4, the catalyst was pretreated with only hydrogen at 300° C. (570° F.) for 1 hour. The resultant catalyst was not selective in that only a 29% hydroqenation of the linear olefin (hexene-1) was obtained with a 39% hydrogenation of the branched olefin (4,4-dimethyl-hexene-1).

The catalyst in Example 5 pretreated with ooth hydrogen and olefin at 275° C. (525° F.) for one hour. This catalyst exhibited very good shape selectivity with a 90% hydrogenation of the linear olefin and less than a 1% hydrogenation of the branched olefin.

In Example 6, catalyst pretreatment involved contact with only olefins, no hydrogen, at 300° C. (570° F.), for 1 hour. The resultant catalyst exhibited some shape selectivity, but not as much as with the dual hydrogen-olefin pretreatment of Example 5.

The catalyst of Example 6 was further treated in Example 7 with both olefins and hydrogen at 400° C. (750° F.) for 17 hours. The result of pretreatment at this elevated temperature was that a very shape selective catalyst was produced, i.e. 100% hydroqenation of the linear olefin as compared to a 1.3% hydrogenation of the branched olefin.

TABLE 1

Effect of Pretreatment on Hydrogenation Selectivity

| Example No. | Pretreatment | Temperature °C. | WHSV | % Hydrogenation hexene-1 | 4,4-diMehexene-1 |
|---|---|---|---|---|---|
| 4 | $H_2$ Only 300° C., 1 hour | 275 | 25 | 29% | 39% |
| 5 | $H_2$ + Olefin Mixture | 275 | 70 | 90% | >1% |
| 6 | Olefins Only 300° C., 1 hour | 254 | 12 | 57% | 19% |
|   |   | 300 | 12 | 95% | 20% |
| 7 | Further treatment at 400° C. in olefins + $H_2$, | 254 | 12 | 100% | 1.3% |

TABLE 1-continued

Effect of Pretreatment on Hydrogenation Selectivity

| Example No. | Pretreatment | Temperature °C. | WHSV | % Hydrogenation hexene-1 | 4,4-diMehexene-1 |
|---|---|---|---|---|---|
| | 17 hours | | | | |

EXAMPLES 8–14

Examples 8–14 demonstrate the improved catalyst attained when back-exchanging cesium ion is used. In Examples 8 to 10, the catalyst utilized is Pt-ZSM-5 prepared according to Example 2. In Examples 11 to 14, the catalyst employed is Cs-Pt-ZSM-5 prepared according to Example 3. Hydrogenation reactions were run in Examples 8 to 14 using the same equipment and experimental procedure of Examples 4–5. The results for these examples is given in Table 2. As shown by Table 2, the cesium containing catalyst was more stable than the catalyst which did not contain cesium.

TABLE 2

| Example No. | Catalyst | Temperature, °C. | Olefin Mixture Used | % Hydrogenation Linear | Branched |
|---|---|---|---|---|---|
| 8 | Pt-ZSM-5 | 150 | octene-1/4,4-diMepentene-1 | 66% | 0% |
| 9 | Pt-ZSM-5 | 295 | heptene-1/4,4-diMepentene-1 | 91.5 | 1.1 |
| 10 | Pt-ZSM-5 | 150 | octene-1/4,4-diMepentene-1 | 16 | 0 |
| | | 220 | octene-1/4,4-diMepentene-1 | 30.7 | 1.4 |
| 11 | Cs-Pt-ZSM-5 | 250 | heptene-1/4,4-diMepentene-1 | 81.9 | 2.5 |
| | | 285 | heptene-1/4,4-diMepentene-1 | 95 | 1.5 |
| 12 | Cs-Pt-ZSM-5 | 250 | hexene-1/4,4-diMehexene-1 | 88.3 | 9.9 |
| | | 275 | hexene-1/4,4-diMehexene-1 | 89.7 | 0.9 |
| 13 | Cs-Pt-ZSM-5 | 275 | hexene-1/6-Meheptene-1 | 14.7 | 4.7 |
| | | 300 | hexene-1/6-Meheptene-1 | 26.7 | 4.8 |
| | | 325 | hexene-1/6-Meheptene-1 | 22.5 | 2.0 |
| 14 | Cs-Pt-ZSM-5 | 305 | hexene-1/6-Meheptene-1 | 25.6 | 2.0 |

EXAMPLES 15–16

The effect of temperature for a non-selective catalyst and the shape selective catalyst representative of this invention is illustrated by Examples 15 and 16. Both the non-selective catalyst used in Example 15 and the shape selective catalyst used in Example 16 were prepared according to Example 3. The non-selective catalyst was prepared with pretreatment with hydrogen only at 300° C. (570° F.), while the shape selective catalyst was pretreated in the presence of an added olefin. Hydrogenation reactions were run in Examples 15 and 16 using the same equipment and experimental procedure of Examples 4 and 5. As shown in Table 3, the non-selective catalyst of Example 15 exhibited decreasing conversions of the linear olefin (hexene) at higher temperatures. In contrast, the activity and selectivity of the shape selective catalyst of Example 16 increased with increasing temperature as shown by the increase in conversion of the linear olefin (hexene).

TABLE 3

Effect of Temperature on Conversion

| Example No. | Catalyst | T. (°C.) | % Hydrogenation hexene-1 | 4,4-diMehexene-1 |
|---|---|---|---|---|
| 15 | non-selective Pt ZSM-5 | 200 | 44.0 | 59.4 |
| | | 250 | 39.5 | 47.9 |
| | | 275 | 29.9 | 38.9 |
| 16 | selective Pt ZSM-5 | 200 | 11.4 | 0.2 |
| | | 250 | 82.7 | 0.3 |
| | | 275 | 90.0 | 0.2 |

EXAMPLE 17

Using a catalyst prepared according to the same procedure of Examples 2 and 3, but with a resultant platinum content of 0.6 wt. % and using the same experimental procedure to conduct hydrogenation reactions as given in Examples 4–7, a different olefinic mixture was tested. The catalyst was pretreated at 400° C. (750° F.) in the presence of this olefin mixture and hydrogen. The results of this example were that selective conversion of pentene-1 (97% hydrogenated) relative to 4,4-dimethylpentene-1 (1.7% hydrogenation) was observed.

EXAMPLES 18–19

Examples 18–19 illustrate the hydrogenation of styrenes. In Example 18, a 0.5% platinum on alumina catalyst obtained from Engelhard Co. was utilized. This catalyst exhibited no shape selectivity in that the precent hydrogenation of styrene and 2-methyl styrene were almost equal. In Example 19, the catalyst utilized was the same catalyst as used previously in Example 17. The pretreatment for both the catalysts in Examples 18 and 19 were exactly the same - olefins and hydrogen with heating to 400° C. (750° F.). The results of Example 19, as shown in Table 4, show that this catalyst is selective in that the linear styrene was 50% hydrogenated, while the non-linear, 2-methylstyrene was only 1.8% hydrogenated.

TABLE 4

Hydrogenation of Styrenes

| Example No. | Catalyst | Pretreatment | T °C. | % Hydrogenation Styrene | 2-Me styrene |
|---|---|---|---|---|---|
| 18 | 0.5% Pt/Al$_2$O$_3$ | Olefins + H$_2$ to 400° C. | 400° | 57% | 58% |
| 19 | Cs-Pt-ZSM-5 | Olefins + H$_2$ to 400° C. | 425° | 50% | 1.8% |

EXAMPLE 20

This example gives the preparation of ZSM-5 zeolite with a crystal size of about 0.02 to 0.05 microns.

An organics salt solution was prepared by mixing 1.6 parts of n-propyl bromide, 1.9 parts of tri-n-propylamine, 3.1 parts of methyl ethyl ketone and 10.4 parts of water. The mixture was reacted at about 100° C. (212° F.) for about 14 hours. The aqueous phase of the reacted mixture is designated Solution A.

A sodium silicate solution was prepared by mixing 16 parts water and 27.7 parts sodium silicate (28.7 wt. % $SiO_2$, 8.9 wt. % $Na_2O$, 62.4% $H_2O$) followd by addition of 0.08 parts Daxad 27 (W. R. Grace Chem. Div.). The solution was cooled to approximately 15° C.

An acid solution was prepared by adding 1 part aluminum sulfate (17.2 wt. % $Al_2O_3$) to 16.4 parts water followed by 2.4 parts NaCl and 2.9 parts of Solution A.

These solutions were mixed in an aqitated vessel while 3.9 parts of NaCl were added. The gel molar ratios expressed as oxides are the following:
$SiO_2/Al_2O_3 = 78.4$
$Na_2O/Al_2O_3 = 49.9$ The gel was agitated for 4 hours at ambient temperature then heated to 95°-110° C. (200°-230° F.) and held for 40 hours with severe agitation. When approximately 65% of the gel was crystallized, the temperature was increased to 150°-160° C. (300°-320° F.) and held there until crystallization was complete.

The zeolite slurry product was diluted with 4-5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the sodium level of the zeolite was less than 1.0 wt. %. The washed zeolite was then filtered, dried and identified as ZSM-5 having a silica/alumina mole ratio of about 70, and a constraint index of about 8.3.

The dried zeolite product was calcined in flowing $N_2$ for 3 hours at 540° C. (1005° F.) then ion exchanged twice with 1 N $NH_4NO_3$ solution (5 parts $NH_4NO_3$ solution/1 part zeolite) for 1 hour at ambient temperature and dried at about 120° C. (250° F.).

EXAMPLES 21-24

The catalyst for Examples 21-24 was prepared using the zeolite prepared according to Example 20 and using the general procedures of Examples 2 and 3 to arrive at a small crystal size Cs-Pt-ZSM-5 with 1.6 weight percent platinum. The catalyst pretreatments and hydrogenation reactions were conducted according to the general experimental procedures given in Examples 4-7. The results for Examples 21-24 are shown in Table 5.

Pretreatment of this catalyst in the presence of olefins and hydrogen did indeed result in a shape selective hydrogenation catalyst, as shown in Table 5. Furthermore, extended thermal treatment in hydrogen at 450° C. (840° F.) enhanced the selectivity, indicating that platinum once formed inside the zeolite does not migrate rapidly to the external surface, even in the case of a small crystal ZSM-5. In a competitive experiment, styrene was completely hydrogenated whereas less than 10% of the 2-methyl styrene was converted. Examples 23-24 illustrate the resistence of the shape selective catalysts of the present invention to poisoning by phosphorous compounds such as phosphine compounds.

TABLE 5

| | Selective Hydrogenation Over a Small Crystal Size Cs—Pt—ZSM-5 Catalyst | | | | |
|---|---|---|---|---|---|
| Example No. | Catalyst Pretreatment | Temperature °C. | WHSV | % Styrene Hydrogenation | % 2-Methylstyrene Hydrogenation |
| 21 | olefin + $H_2$ to 450° C. | 350° | 8 | 97% | 18% |
| 22 | additional 16 hours in $H_2$ at 450° C. | 350° | 20 | >99% | 9% |
| 23 | addition of 50 mg tri-p-tolyl phosphine | 350° 350° | 20 8 | 79% 93% | 0.5% 1% |
| 24 | second addition of 50 mg phosphine | 350° | 8 | 64% | 0.5% |

EXAMPLES 25-28

A CsPt ZSM-5 catalyst was prepared according to the general procedure of Example 2 with a resultant platinum content of 1.5 wt. %. The catalyst was pretreated in the absence of hydrogen with hexene-1 and nitrogen (partial pressure of hexene was about 150 torr) at 450° C. (840° F.). The catalyst was employed in hydroqenation reactions at 300° C. (570° F.) 30 WHSV with $H_2/HC = 20$. Example 25 shows the results for the employment of the aforementioned catalyst with Examples 26-27 representing further treatment of the catalyst with hydrogen present. Example 28 shows a pretreatment with a paraffin (hexane) which gives a non-shape selective catalyst and is shown for comparison purposes. Results for Examples 25-28 are given hereinbelow in Table 6.

TABLE 6

| EXAMPLE NO. | CATALYST PRETREATMENT | PENTENE-1 | % HYDROGENATION 4,4,DIMETHYL-PENTENE-1 |
|---|---|---|---|
| 25 | Hexene-1 + $N_2$ to 450° C. | 89% | 18% |
| 26 | Additional 17 hrs in $H_2$ only at 400° C. | 86% | 4.7% |
| 27 | Additional 2 hrs in $H_2$ only at 450° C. | 53% | trace |
| 28 | Hexene + $H_2$ to 350° C. | 34% | 25% |

EXAMPLES 29-34

Examples 29-34 illustrate shape selective reactions which employ as a catalyst a shape selective Pt-ZSM-5 catalyst analogous to the catalyst of Example 1 but having a significantly higher silica/alumina ratio.

EXAMPLE 29

A catalyst composite is prepared by reducing a ZSM-5 catalyst having an $SiO_2/Al_2O_3$ ratio of about 7000 and containing about 0.54% platinum. Reduction is carried out in a stream of nitrogen and hexene-1, while the temperature is raised from room temperature to 450° C. at the rate of 2° C./minute.

EXAMPLE 30

Passing n-dodecane in hydrogen over the catalyst of Example 29 at 400° C. and 0.4 WHSV results in 50% conversion to a mixture of products which include: (1) normal paraffins, including n-undecane and n-decane, as well as methane and ethane—all products characteristic of metal induced cracking; (2) one major cycloparaffin, believed to be n-heptyl cyclopentane; (3) some skeletal isomers of dodecane, mainly 2-methyl and 3-methyl undecane; and (4) aromatics, predominantly n-hexylbenzene.

Conversion of n-nonane under similar conditions produces mainly iso-nonanes, n-octane, n-butylcyclopentane, n-propylbenzene, indane, and several $C_8$ and $C_9$ aromatics.

Replacement of hydrogen with nitrogen results in an increase in dehydrocyclization and a decrease in hydrocracking. In addition, hydrogen is a major product obtained. Thus, using n-octane as the feed at 465° C., the following conversion results are realized.

|  | % Conversion | $C_3^*$ | Ethylbenzene* | o-xylene* |
|---|---|---|---|---|
| in $H_2$ | 42 | 2.6 | 9.6 | 7.2 |
| in $N_2$ | 80 | 1.6 | 36.6 | 19.5 |

*Component in effluent

EXAMPLE 31

A mixture containing n-hexadecane, a linear paraffin, and 2,6,10,14-tetramethyl pentadecane is passed over the catalyst of Example 29 at 450° C. The normal paraffin is 65% converted, whereas only 8% conversion of the branched hydrocarbon is observed.

EXAMPLE 32

An equimolar mixture of 1,2-dimethylcyclohexane and 1,4-dimethylcyclohexane (mixture of isomers) is passed over the catalyst of Example 29 in hydrogen at 400° C. The effluent contains 29.7% para-xylene and only 12.5% ortho-xylene, reflecting a 3-fold selectivity factor in favor of the paraisomer.

EXAMPLE 33

When 20 mg tri-p-tolylphosphine is added to the reaction of Example 32, the concentration of both xylenes in the effluent decreases to 9.8% para and 0.7% ortho, corresponding to a selectivity factor of 15. Further addition of tri-p-tolylphosphine has no effect on conversions or selectivity.

EXAMPLE 34

To illustrate shape selective dewaxing and reforming, an Arab Light distillate, 400° to 650° F., containing mainly $C_{12}$–$C_{18}$ hydrocarbons, is passed over the catalyst of Example 29 at 465° C. and 0.4 WHSV Analysis of the product reveals extensive decrease in the normal paraffins and an increase in aromatic content. The pour point of the product is reduced to $-42°$ C. from the original $-20°$ C.

What is claimed is:

1. The process for conducting shape selective catalytic isomerization of alkylaromatic compounds in a feedstock comprising alkylaromatic hydrocarbon compounds which comprises contacting said feedstock under conversion conditions including a temperature of from about 260° C. to about 600° C., a pressure of from about 240 kPa to about 7000 kPa and a hydrogen/feedstock alkylaromatic hydrocarbon mole ratio of from about 1 to about 20 with a shape selective metallic catalyst prepared by incorporating a metallic catalyst component selected from Group VIII metals of the Periodic Table and combinations thereof into a zeolite, said zeolite having a silica to alumina mole ratio of at least 12 and a constraint index of 1 to 12, followed by reduction of the metal catalyst component to a valence of zero in an atmosphere of one or more unsaturated hydrocarbon compounds and hydrogen at a temperature in the range of from about 100° C. to about 500° C. wherein said one or more unsaturated hydrocarbon compounds are maintained in said atmosphere at a concentration between 10% and 50% until said reduction of the metal catalyst component to a valence of zero is complete, said shape selective metallic catalyst being further characterized by having the position of said metallic catalyst component inside rather than outside said zeolite.

2. The process of claim 1 wherein said alkylaromatic hydrocarbon compound are selected from the group consisting of xylenes and ethylbenzene and mixtures thereof.

3. The process of claim 1, wherein said zeolite is selected from the group consisting of those having the structure of ZSM-5, ZSM-11, ZSM-5/ZSM-11 intermediate, ZSM-12, ZSM-23, ZSM-35, ZSM-38, and ZSM-48.

4. The process of claim 3, wherein said zeolite is ZSM-5 or ZSM-11.

5. The process of claim 1, wherein said metallic catalyst component is selected form the group consisting of platinum, palladium, nickel and combinations thereof.

6. The process of claim 5, wherein said metallic catalyst component is platinum.

7. The process of claim 1, wherein said unsaturated hydrocarbon compound is an olefin.

8. The process of claim 1, wherein the silica to alumina mole ratio of the zeolite is at least about 500:1.

9. The proceas of claim 1, wherein said metallic catalyst component is incorporated into said zeolite by ion exchange.

10. The process of claim 1, which further comprises back exchanging a cation into said catalyst prior to the reduction.

11. The process of claim 10, wherein said cation is cesium or potassium.

12. The process of claim 1, wherein the selectivity of the catalyst is further increased by treating said catalyst with a catalyst poison phosphorus-containing compound which is larger in size than the pores of said zeolite.

* * * * *